United States Patent [19]

Maurer et al.

[11] 4,014,996
[45] Mar. 29, 1977

[54] O-ALKYL-O-PYRIMIDIN (2)YL-THIONOPHOSPHONIC ACID ESTERS

[75] Inventors: Fritz Maurer; Hans-Jochem Riebel, both of Wuppertal; Wolfgang Behrenz, Overath-Steinenbrueck; Ingeborg Hammann, Cologne; Bernhard Homeyer, Opladen, all of Germany

[73] Assignee: Bayer Aktiengesellschaft, Leverkusen, Germany

[22] Filed: Aug. 25, 1975

[21] Appl. No.: 607,327

[30] Foreign Application Priority Data

Aug. 24, 1974 Germany ............................ 2440677

[52] U.S. Cl. ............................ 424/200; 260/251 P; 260/251 R
[51] Int. Cl.² ...................... C07F 9/65; A01N 9/36
[58] Field of Search ................ 260/251 P; 424/200

[56] References Cited

UNITED STATES PATENTS

| 3,159,630 | 12/1964 | Rigterink ........................ 260/256.4 |
| 3,216,894 | 9/1965 | Lorenz et al. .............. 260/251 P X |
| 3,741,968 | 6/1973 | Haubein ........................ 260/251 P |

*Primary Examiner*—Donald G. Daus
*Assistant Examiner*—Diana G. Rivers
*Attorney, Agent, or Firm*—Burgess, Dinklage & Sprung

[57] ABSTRACT

O-Alkyl-O-pyrimidin(2)yl-thionophosphonic acid esters of the formula

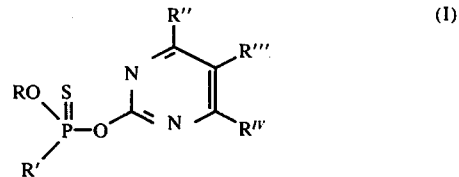

in which
R is alkyl with 1 to 6 carbon atoms,
R' is alkyl with 1 to 6 carbon atoms or phenyl,
R'' and R$^{IV}$ each independently is hydrogen or alkyl with 1 to 4 carbon atoms, and
R''' is halogen or hydrogen.

which possess insecticidal, acaricidal and nematocidal properties.

11 Claims, No Drawings

O-ALKYL-O-PYRIMIDIN (2)YL-THIONOPHOSPHONIC ACID ESTERS

The present invention relates to and has for its objects the provision of particular new O-alkyl-O-pyrimidin(2)yl-thionophosphonic acid esters, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from Patent Specification No. 3,741,968 and German Patent Specification No. 947,208 that pyrimidinylthionophosphoric acid esters, for example 0,0-dimethyl-(Compound A) and 0,0-diethyl-0-[pyrimidin(2)yl]-thionophosphoric acid ester (Compound B) and 0,0-diethyl-0-[2-isopropyl-4-methyl-pyrimidin(6)yl]-thionophosphoric acid ester (Compound C) have insecticidal and acaricidal properties. The present invention provides pyrimidinylthionophosphonic acid esters of the general formula

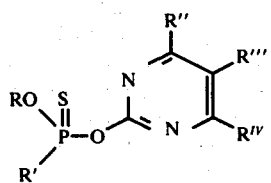

in which
R is alkyl with 1 to 6 carbon atoms,
R' is alkyl with 1 to 6 carbon atoms or phenyl,
R'' and $R^{IV}$ each independently is hydrogen or alkyl with 1 to 4 carbon atoms, and
R''' is halogen or hydrogen.

Preferably, R represents straight-chain or branded alkyl with 1 to 4 carbon atoms, R' represents straight-chain or branched alkyl with 1 to 4 carbon atoms or phenyl, R'' and $R^{IV}$ represent hydrogen, methyl or ethyl, and R''' represents hydrogen, chlorine or bromine.

Surprisingly, the pyrimidinylthionophosphonic acid esters according to the invention have a better insecticidal (including soil-insecticidal), acaricidal and nematocidal action than the previously known compounds of analogous structure and of the same type of action. The new products are not only active against foliage insects and soil insects, mites and nematodes, but also against hygiene pests and pests of stored products. Accordingly, they represent a genuine enrichment of the art.

The invention also provides a process for the production of a pyrimidinylthionophosphonic acid ester of the formula (I) in which an O-alkylthionophosphonic acid ester halide of the general formula

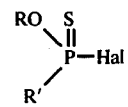

in which
R and R' have the above-mentioned meanings and
Hal represents halogen, preferably chlorine, is reacted with a 2-hydroxypyrimidine derivative of the general formula

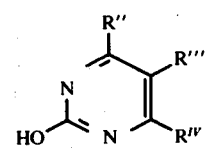

in which R'', R''' and $R^{IV}$ have the above-mentioned meanings, in the form of the free base or the hydrochloride or an alkali metal salt, alkaline earth metal salt or ammonium salt.

The reaction may of course be carried out in the presence of an acid acceptor when the 2-hydroxypryimidine derivative is one which makes this appropriate.

If, the example, O-tert.-butyl-thionoethanephosphonic acid ester chloride and 2-hydroxy-5-iodo-pyrimidine are used as starting materials, the course of the reaction can be represented by the following formula scheme:

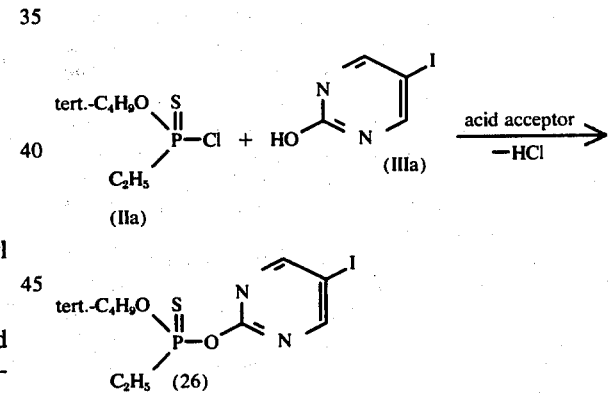

The O-alkylthionophosphonic acid ester halides (II) to be used as starting materials are known from the literature and can be prepared in accordance with generally customary processes.

The following may be mentioned individually as examples of these halides: O-methyl-, O-ethyl-, O-n-propyl-, O-iso-propyl-, O-n-butyl-, O-sec.-butyl-, O-iso-butyl- and O-tert.-butyl-methane, -ethane-, -n-propane-, -iso-propane-, -n-butane-, -iso-butane-, -sec.-butane-, -tert.-butane and -phenyl-thionophosphonic acid ester chloride.

The 2-hydroxypyrimidine derivatives (III), some of which are new, can be prepared in accordance with processes known from the literature, for example by reacting 1,1,3,3-tetraalkoxypropane and urea, in alcoholic solution, with hydrogen chloride as taught in Patent Specification No. 3,741,968, the disclosure of which is incorporated herein by reference; the halogenated derivatives can be prepared therefrom by reaction with halogenating agents, for example bromine.

The following may be mentioned individually as examples of 2-hydroxypyrimidine derivatives (III) for use in the process of the invention: 4,6-dimethyl-, 4,6-diethyl-, 4-methyl-, 4-ethyl-, 5-chloro- and 5-bromo-2-hydroxypyrimidine and 2-hydroxypyrimidine.

The reaction according to the invention is preferably carried out in the presence of a solvent which term includes a mere diluent. Practically all inert organic solvents can be used for this purpose. These include, in particular, aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alakli metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 100° C, preferably at 40° to 55° c.

The reaction is in general allowed to take place under normal pressure.

In carrying out the process according to the invention, the reactants are in general employed in equimolar ratios. The reaction is preferably carried out at the temperatures indicated in the presence of one of the above-mentioned solvents or diluents and, when appropriate, in the presence of an acid acceptor. After completion of the reaction, the mixture may be worked up in the usual manner, for example by adding an organic solvent to the reaction mixture and washing, drying and distilling the organic phase.

The new compounds are frequently obtained in the form of oils which in most cases cannot be distilled without decomposition but may be freed from the last volatile constituents by so-called "slight distillation", that is to say by prolonged heating under reduced pressure to moderately elevated temperatures, and they may be purified in this way. They are characterized by the refractive index. Some compounds are obtained in a crystalline form of sharp melting point.

As has already been mentioned, the pyrimidinylthionophosphonic acid esters according to the invention are distinguished by an excellent foliage-insecticidal and soil-insecticidal, acaricidal and nematocidal activity. They are active against plant pests, hygiene pests and pests of stored products. They have a good action both against sucking and against biting insects and mites.

For this reason, the compounds according to the invention can be employed successfully as pesticides in plant protection and in the hygiene field and the field of protection of stored products.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*), and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrostis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuehniella*) and greater wax moth (*Galleria mellonella*).

Also to be classed with the biting insects are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (*Tetranychidae*) such as the two-spotted spider mite(*Tetranychus urticae*) and the European red mite (*Paratetranychus pilosus* = *Panonychus ulmi*, gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide esters of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, and nematocides, fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematode, the preparations are generally applied to an area of argriculture in amounts of 1 to 100 kg of active compound per hectare, and are then incorporated into the soil.

Furthermore, the present invention contemplates methods of selectively killing, combating or controlling pests, e.g. insects, acarids, nematodes comprises applying to at least one of correspondingly (a) such insects (b) such acarids, (c) such nematodes (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Critical concentration test/soil insects
Test insect: *Phorbia antiqua* grubs
Solvent: 3 parts of weight of acetone
Emulsifier: 1 part of weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all tests insects had been killed and was 0% if exactly as many test insects were still alive as in the case of the untreated control.

The active compounds, amounts used and results can be seen from the table which follows:

TABLE 1

Soil insecticide test/*Phorbia antiqua* grubs in the soil

| Active compound | Degree of destruction in % at an active compound concentration of 2.5 ppm |
|---|---|
| [B] | 0 |
| [A] | 0 |
| (4) | 100 |
| (6) | 100 |
| (1) | 100 |
| (9) | 100 |
| (10) | 100 |
| (12) | 100 |

TABLE 1-continued

Soil insecticide test/*Phorbia antiqua* grubs in the soil

| Active compound | Degree of destruction in % at an active compound concentration of 2.5 ppm |
|---|---|
| (13) Cl-pyridine-N=C-O-P(=S)(OC₂H₅)(C₆H₅) | 100 |
| (14) Br-pyridine-N=C-O-P(=S)(OC₂H₅)(C₂H₅) | 100 |
| (15) Br-pyridine-N=C-O-P(=S)(OC₃H₇-n)(C₂H₅) | 100 |
| (16) pyridine-N=C-O-P(=S)(CH₃)(OC₃H₇-iso) | 100 |
| (18) Br-pyridine-N=C-O-P(=S)(CH₃)(OC₃H₇-iso) | 100 |

EXAMPLE 2

Critical concentration test/soil insects
Test insect: *Tenebrio molitor* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

TABLE 2

Soil insecticide test/*Tenebrio molitor* larvae in the soil

| Active compound | Degree of destruction in % at an active compound concentration of 10 ppm |
|---|---|
| [A] pyridine-N=C-O-P(=S)(OCH₃)(OCH₃) | 0 |
| (4) CH₃-pyridine-N=C-O-P(=S)(OC₃H₇-n)(C₂H₅) | 100 |

TABLE 2-continued

Soil insecticide test/*Tenebrio molitor* larvae in the soil

| Active compound | Degree of destruction in % at an active compound concentration of 10 ppm |
|---|---|
| (6) [structure: 4-methylpyrazine with O-P(=S)(OC₂H₅)(C₂H₅)] | 100 |
| (1) [structure: pyrazine with O-P(=S)(OC₂H₅)(C₂H₅)] | 100 |
| (12) [structure: pyrazine with O-P(=S)(OC₃H₇-n)(C₂H₅)] | 100 |
| (13) [structure: chloropyrazine with O-P(=S)(OC₂H₅)(phenyl)] | 100 |
| (14) [structure: bromopyrazine with O-P(=S)(OC₂H₅)(C₂H₅)] | 100 |
| (15) [structure: bromopyrazine with O-P(=S)(OC₃H₇-n)(C₂H₅)] | 100 |
| (16) [structure: pyrazine with O-P(=S)(CH₃)(OC₃H₇-iso)] | 100 |

EXAMPLE 3

Critical concentration test
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The treated soil was filled into pots, lettuce was sown in and the pots were kept at a greenhouse temperature of of 27° C.

After 4 weeks, the lettuce roots were examined for infestation with nematodes (root knots), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following Table 3:

TABLE 3

Nematocide test/*Meloidogyne incognita*

| Active compound | Degree of destructon in % at an active compound concentration of 10 ppm |
|---|---|
| [A] 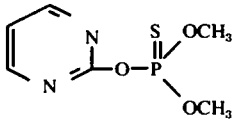 | 0 |
| [C] 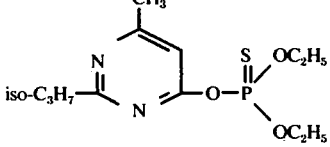 | 0 |
| (4) 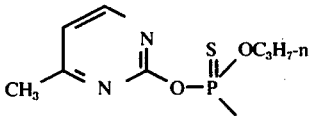 | 100 |
| (6) 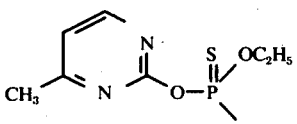 | 100 |
| (1) 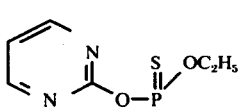 | 100 |
| (10) 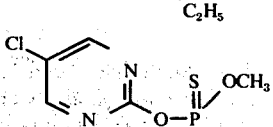 | 100 |
| (12)  | 100 |
| (14) 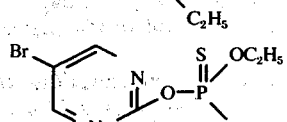 | 100 |
| (15) 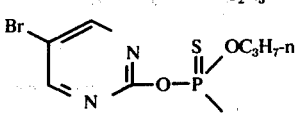 | 100 |

EXAMPLE

Drosophila test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm³ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following Table 4:

TABLE 4

(*Drosophila* test)

| Active compound | | Active compound concentration in % by weight | Degree of destruction in % after 1 day |
|---|---|---|---|
| [A] | pyrimidine-O-P(=S)(OCH₃)(OCH₃) | 0.001 | 100 |
|  |  | 0.0001 | 0 |
| (5) | Br-pyrimidine-O-P(=S)(C₂H₅)(OCH₃) | 0.0001 | 100 |
| (10) | Cl-pyrimidine-O-P(=S)(OCH₃)(C₂H₅) | 0.0001 | 100 |
| (11) | Cl-pyrimidine-O-P(=S)(OC₂H₅)(C₂H₅) | 0.0001 | 100 |
| (14) | Br-pyrimidine-O-P(=S)(OC₂H₅)(C₂H₅) | 0.0001 | 100 |

EXAMPLE 5

Doralis test (Systemic action)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that the preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following Table 5:

TABLE 5

(*Doralis* test/systemic action)

| Active compound | | Active compound concentration in % by weight | Degree of destruction in % after 4 days |
|---|---|---|---|
| [C] | iso-C₃H₇-pyrimidine(CH₃)-O-P(=O)(OC₂H₅)(OC₂H₅) | 0.1 | 100 |
|  |  | 0.01 | 0 |
| (3) | pyrimidine-O-P(=S)(OCH₃)(C₂H₅) | 0.01 | 100 |

TABLE 5-continued (*Doralis* test/systemic action)

| Active compound | Active compound concentration in % by weight | Degree of destruction in % after 4 days |
|---|---|---|
| (4) [structure: CH₃–C(=N–)–CH=CH–O–P(=S)(OC₃H₇-n)(C₂H₅)] | 0.01 | 95 |
| (11) [structure: Cl–CH=CH–C(=N–)–... O–P(=S)(OC₂H₅)(C₂H₅)] | 0.01 | 100 |
| (16) [structure: pyridine-type with O–P(=O)(CH₃)(OC₃H₇-iso)] | 0.01 | 100 |
| (19) [structure: (CH₃)₂C=CH–C(=N–)–O–P(=O)(C₂H₅)(OC₂H₅)] | 0.01 | 100 |

EXAMPLE 6

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the degree of destruction was determined as a percentage: 100% means that all the spider mites were killed; 0% means that none of the spider mites were killed.

The active compounds, the concentrations of the active compounds, the evaluation times and the results can be seen from the following Table 6:

TABLE 6

(*Tetranychus* test)

| Active compound | Active compound concentration in % by weight | Degree of destruction in % after 2 days |
|---|---|---|
| [C] [structure with iso-C₃H₇, CH₃, and O–P(=S)(OC₂H₅)₂] | 0.1<br>0.01 | 100<br>0 |
| (10) [structure: Cl-substituted with O–P(=S)(OCH₃)(C₂H₅)] | 0.1<br>0.01 | 100<br>80 |
| (14) [structure: Br-substituted with O–P(=S)(OC₂H₅)(C₂H₅)] | 0.1<br>0.01 | 100<br>99 |

TABLE 6-continued (*Tetranychus* test)

| Active compound | Active compound concentration in % by weight | Degree of destruction in % after 2 days |
|---|---|---|
| (15) Br-[pyridine]-N=C(O-P(=S)(OC$_3$H$_7$-n)(C$_2$H$_5$)) | 0.1<br>0.01 | 100<br>100 |
| (18) Br-[pyridine]-N=C(O-P(=S)(CH$_3$)(OC$_3$H$_7$-iso)) | 0.1<br>0.01 | 100<br>99 |

The active compounds, the concentrations of the active compounds, the evaluation times and the results can be seen from Table 7 which follows:

TABLE 7

Long-term action after spraying with 0.05% by weight of active compound
(*Plutella maculipennis* on *Brassica oleracea*)

| Active compound | % destruction after | | |
|---|---|---|---|
| | 4 days | 8 days | 11 days |
| [C] iso-C$_3$H$_7$-N=C(CH$_3$)-CH=CH-C(=N)-O-P(=S)(OC$_2$H$_5$)(OC$_2$H$_5$) | 50 | 0 | |
| (8) Br-[pyridine]-N=C-O-P(=S)(OC$_2$H$_5$)(C$_6$H$_5$) | 100 | 100 | 100 |
| (13) Cl-[pyridine]-N=C-O-P(=S)(OC$_2$H$_5$)(C$_6$H$_5$) | 100 | 100 | 100 |

EXAMPLE 7

Plutella test (long-term action after spraying)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage plants (*Brassica oleracea*) which were about 10-15 cm high were sprayed with the preparation of active compound until dripping wet.

After the specified periods of time, the plants were infested with caterpillars of the diamond-back moth (*Plutella maculipennis*). After 3 days, the destruction was determined as a percentage. 100% means that all the caterpillars had been killed; 0% means that none of the caterpillars had been killed.

EXAMPLE 8

Plutella test (long-term action after watering)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage plants (*Brassica oleracea*) were each watered with 50 ml of the preparation of active compound so that this preparation penetrated into the soil without wetting the leaves of the cabbage plants. The active compound was taken up by the cabbage plants from the soil and thus passed to the leaves.

After the specified periods of time, the plants were infested with caterpillars of the diamond-back moth (*Plutella maculipennis*). After 3 days, the destruction was determined as a percentage. 100% means that all the caterpillars had been killed. 0% means that none of the caterpillars had been killed.

The active compounds, the concentrations of the active compounds, the evaluation times and the results can be seen from Table 8 which follows:

TABLE 8

Long-term action after watering with
0.025% by weight of active compound
(*Plutella maculipennis* on *Brassica oleracea*)

| Active compound | % destruction after | | | |
|---|---|---|---|---|
| | 4 days | 8 days | 11 days | 15 days |
| [C] 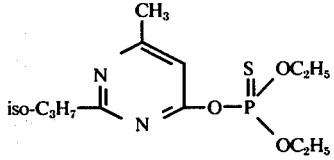 | 100 | 90 | 0 | |
| (3) 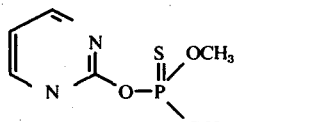 | 100 | 100 | 100 | 100 |
| (4) 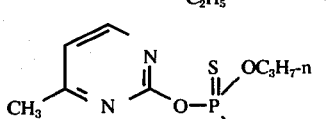 | 100 | 100 | 100 | 100 |
| (5) 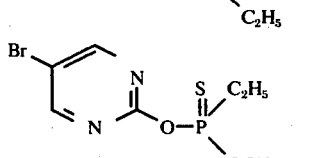 | 100 | 100 | 100 | 100 |
| (1) 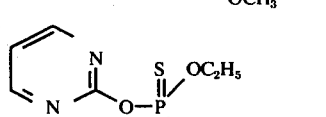 | 100 | 100 | 100 | 100 |
| (9) 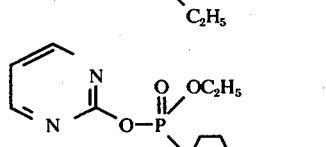 | 100 | 100 | 100 | 90 |
| (10) 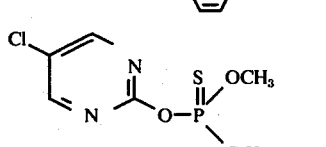 | 100 | 100 | 100 | 100 |
| (11) 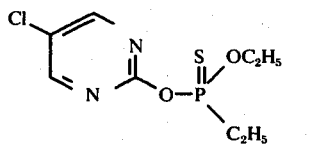 | 100 | 100 | 100 | 100 |
| (12) 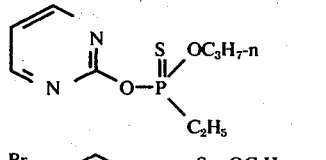 | 100 | 100 | 100 | 100 |
| (14) 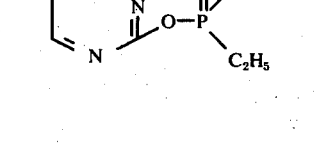 | 100 | 100 | 100 | 100 |

TABLE 8-continued

Long-term action after watering with
0.025% by weight of active compound
(*Plutella maculipennis* on *Brassica oleracea*)

| Active compound | % destruction after | | | |
|---|---|---|---|---|
| | 4 days | 8 days | 11 days | 15 days |
| (15) [Br-pyridinyl-O-P(=S)(OC$_3$H$_7$-n)(C$_2$H$_5$)] | 100 | 100 | 100 | 100 |

EXAMPLE 9

LT$_{100}$ test for Diptera

Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there is 100% destruction can be seen from the following Table 9.

TABLE 9

(LT$_{100}$ test for diptera/*Musca domestica*)

| Active compound | Active compound concentration of the solution in % by weight | LT$_{100}$ in min. (') or hours (hr) |
|---|---|---|
| [B] pyridinyl-O-P(=S)(OC$_2$H$_5$)(OC$_2$H$_5$) | 0.02 | 6 hrs |
| (1) pyridinyl-O-P(=S)(OC$_2$H$_5$)(C$_2$H$_5$) | 0.02 | 120' |
| (3) pyridinyl-O-P(=S)(OCH$_3$)(C$_2$H$_5$) | 0.02 | 80' |
| (11) Cl-pyridinyl-O-P(=S)(OC$_2$H$_5$)(C$_2$H$_5$) | 0.02 | 80' |
| (10) Cl-pyridinyl-O-P(=S)(OCH$_3$)(C$_2$H$_5$) | 0.02 | 95' |
| (14) Br-pyridinyl-O-P(=S)(OC$_2$H$_5$)(C$_2$H$_5$) | 0.02 | 110' |

TABLE 9-continued (LT$_{100}$ test for diptera/*Musca domestica*)

| Active compound | Active compound concentration of the solution in % by weight | LT$_{100}$ in min. (') or hours (hr) |
|---|---|---|
| (5) [structure with Br, S, C$_2$H$_5$, OCH$_3$] | 0.02 | 120' |
| (6) [structure with CH$_3$, S, OC$_2$H$_5$, C$_2$H$_5$] | 0.02 | 195' |
| (2) [structure with CH$_3$, S, OCH$_3$, C$_2$H$_5$] | 0.02 | 100' |
| (24) [structure with Cl, CH$_3$, CH$_3$, S, C$_2$H$_5$, OCH$_3$] | 0.02 | 50' |
| (25) [structure with Cl, CH$_3$, CH$_3$, S, CH$_3$, OC$_3$H$_7$-iso] | 0.02 | 90' |

A process for making the novel compounds is shown in the following illustrative example:

EXAMPLE 10 a. The following exemplifies the preparation of the 2-hydroxypyrimidine derivatives (III) required as starting materials:

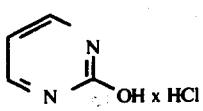

90 g (0.55 mole) of 1,1,3,3-tetra-methoxypropane were added to a solution of 30 g (0.5 mole) of urea in 350 ml of warm ethanol, and 100 ml of concentrated hydrochloric acid were added dropwise to this mixture over the course of 1 to 2 hours. While doing so, the temperature was kept at between 30 and 40° C; thereafter the mixture was stirred for a further 5 hours, at room temperature. After adding 500 ml of ether, the reaction product was filtered off. This gave 48.5 g (79% of theory) of 2-hydroxypyrimidine hydrochloride in the form of a yellow powder of melting point 198 to 201° C (with decomposition.)

The following 2-hydroxypyrimidine derivatives were prepared analogously:

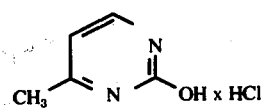

94% yield; melting point 236° C (decomposition)

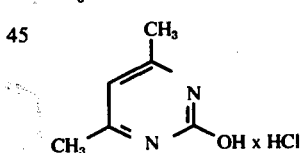

80% yield; melting point 240° C (decomposition)

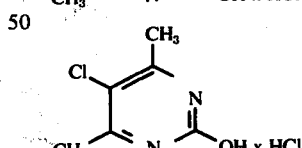

72% yield; melting point 210° C

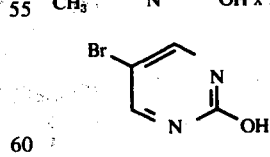

84 g (0.525 mole) of bromine were added to a solution of 66 g (0.5 mole) of 2-hydroxypyrimidine hydrochloride in 80 ml of water at room temperature. The mixture was then warmed to 70°–80° C for 15 minutes, after which it was cooled to 5°–10° C. The product which had precipitated was filtered off and rinsed with water. This gave 56 g (64% of theory) of 2-hydroxy-5-bromo-pyrimidine in the form of a colorless powder of melting point 250° C.

The following was prepared analogously:

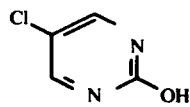

45% yield; melting point 218° C (decomposition)

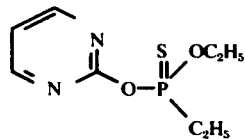

17.2 g (0.1 mole) of O-ethyl-ethanethionophosphonic acid ester chloride were added to a suspension of 13.2 g (0.1 mole) of 2-hydroxypyrimidine hydrochloride and 34.5 g (0.25 mole) of potassium carbonate in 300 ml of acetonitrile. Thereafter, the reaction mixture was stirred for 3 hours at 50° C and then cooled to 20° C, and 600 ml of toluene were added. The mixture was extracted by shaking with twice 500 ml of water and the organic phase was separated off and dried over sodium sulfate. The solvent was then stripped off in vacuo and the residue was subjected to incipient distillation at 80° C. This gave 20 g (86% of theory) of O-ethyl-O-pyrimidin(2)yl-ethanethionophosphonic acid ester in the form of a yellow oil of refractive index $n^{22}_D$: 1.5283.

The following compounds were prepared analogously:

| Compound No. | Structure | Yield (% of theory) | Physical data (melting point ° C; refractive index) |
|---|---|---|---|
| 2 | 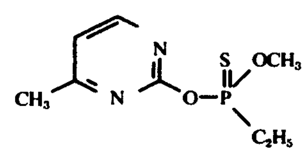 | 77 | $n_D^{26}$: 1.5310 |
| 3 | 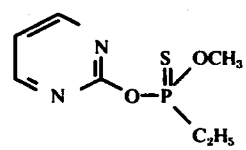 | 78 | $n_D^{24}$: 1.5358 |
| 4 | 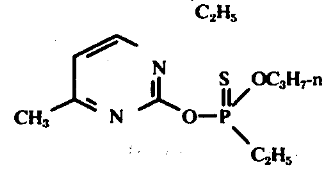 | 85 | $n_D^{25}$: 1.5194 |
| 5 | 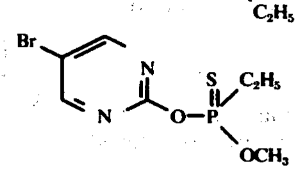 | 54 | 56 |
| 6 | 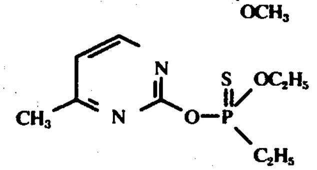 | 89 | $n_D^{23}$: 1.5203 |
| 7 | 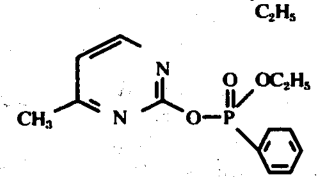 | 85 | $n_D^{23}$: 1.5774 |
| 8 | 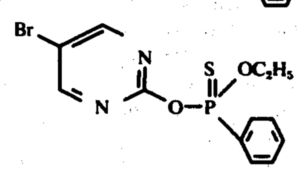 | 75 | $n_D^{22}$: 1.6006 |
| 9 | 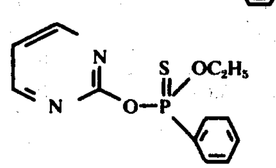 | 79 | $n_D^{22}$: 1.5833 |

-continued
| Compound No. | Structure | Yield (% of theory) | Physical data (melting point ° C; refractive index) |
|---|---|---|---|
| 10 | 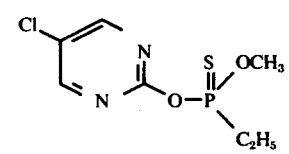 | 75 | $n_D^{24}$: 1.5468 |
| 11 | 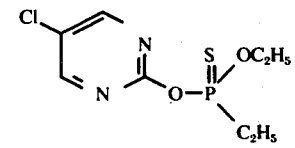 | 79 | $n_D^{24}$: 1.5363 |
| 12 | 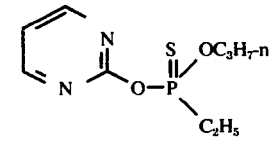 | 89 | $n_D^{24}$: 1.5250 |
| 13 | 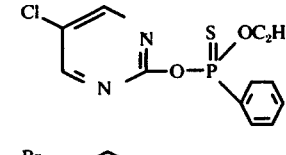 | 73 | $n_D^{24}$: 1.5909 |
| 14 | 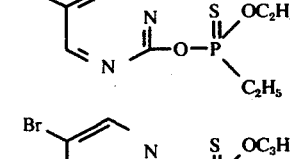 | 64 | $n_D^{24}$: 1.5472 |
| 15 | 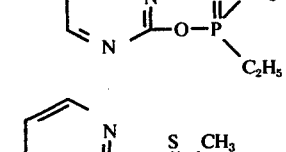 | 62 | $n_D^{24}$: 1.5513 |
| 16 | 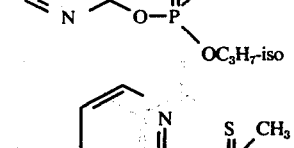 | 48 | $n_D^{27}$: 1.5188 |
| 17 | 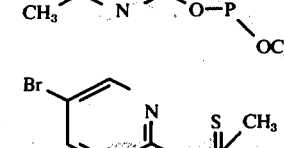 | 52 | $n_D^{26}$: 1.5140 |
| 18 | 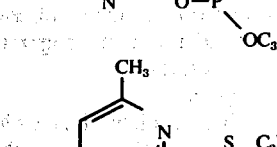 | 68 | $n_D^{26}$: 1.5407 |
| 19 | 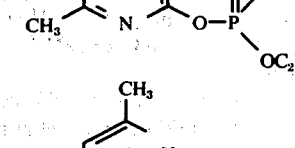 | 73 | $n_D^{24}$: 1.5169 |
| 20 | 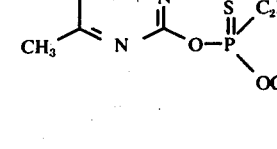 | 59 | $n_D^{24}$: 1.5128 |

-continued

| Compound No. | Structure | Yield (% of theory) | Physical data (melting point ° C; refractive index) |
|---|---|---|---|
| 21 | (structure) | 52 | $n_D^{24}$: 1.5851 |
| 25 | (structure) | 58 | $n_D^{23}$: 1.5240 |
| 22 | (structure) | 78 | $n_D^{23}$: 1.5085 |
| 23 | (structure) | 67 | 54 – 56 |
| 24 | (structure) | 75 | $n_D^{24}$: 1.5383 |

Other compounds which can be similarly prepared include:

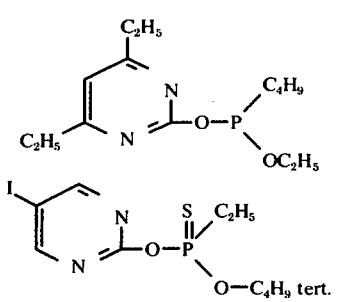

and the like.

It will be appreciated the the instant specification and examples are set forth by way of illustration and not limitation, and that various modifications and changes may be made without departing from the spirit and scope of the present invention.

What is claimed is

1. An O-alkyl-O-pyrimidin(2)yl-thionophosphonic acid ester of the formula

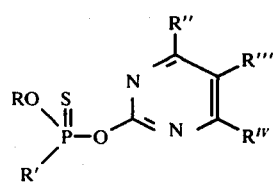

in which

R is alkyl with 1 to 6 carbon atoms,
R' is alkyl with 1 to 6 carbon atoms or phenyl,
R" and $R^{IV}$ each independently is hydrogen or alkyl with 1 to 4 carbon atoms, and
R'" is halogen or hydrogen 2. A compound according to claim 1 in which R is alkyl with 1 to 4 carbon atoms, R' is alkyl with 1 to 4 carbon atoms or phenyl, R" and $R^{IV}$ each independently is hydrogen, methyl or ethyl, and R'" is hydrogen, chlorine or bromine.

3. A compound according to claim 1, wherein such compound is O-ethyl-O-pyrimidin(2)yl-ethanethionophosphonic acid ester of the formula

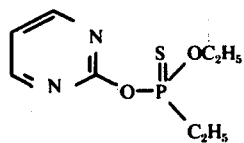

4. A compound according to claim 1, wherein such compound is O-ethyl-O-[5-bromo-pyrimidin(2)yl]-benzenethionophosphonic acid ester of the formula

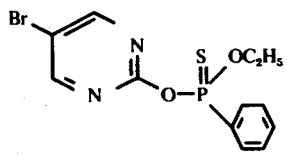

5. A compound according to claim 1, wherein such compound is O-ethyl-O-pyrimidin(2)yl-benzenethionophosphonic acid ester of the formula

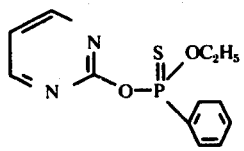

6. A compound according to claim 1, wherein such compound is O-methyl-O-[5-chloro-pyrimidin(2)yl]-ethanethionophosphonic acid ester of the formula

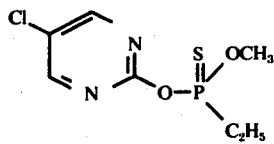

7. A compound according to claim 1, wherein such compound is O-ethyl-O-[5-bromo-pyrimidin(2)yl]-ethanethionophosphonic acid ester of the formula

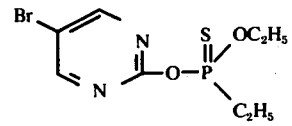

8. A compound according to claim 1, wherein such compound is O-n-propyl-O-[5-bromo-pyrimidin(2)yl]-ethanethionophosphonic acid ester of the formula

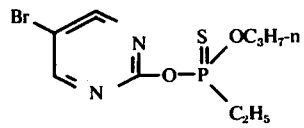

9. An insecticidal, acaricidal or nematocidal composition containing as active ingredient an insecticidally, acaricidally or nematocidally effective amount of a compound according to claim 1 in admixture with a diluent.

10. A method of combating insect, acarid or nematode pests which comprises applying to the pests or a habitat thereof an insecticidally, acaricidally or nematocidally effective amount of a compound according to claim 1.

11. The method according to claim 10 in which said compound is O-ethyl-O-pyrimidin(2)yl-ethanethionophosphonic acid ester,
   O-ethyl-O-[5-bromo-pyrimidin(2)yl]-benzenethionophosphonic acid ester,
   O-ethyl-O-pyrimidin(2)yl-benzenethionophosphonic acid ester,
   O-methyl-O-[5-chloro-pyrimidin(2)yl]-ethanethionophosphonic acid ester,
   O-ethyl-O-[5-bromo-pyrimidin(2)yl]-ethanethionophosphonic acid ester,
   O-n-propyl-O-[5-bromo-pyrimidin(2)yl]-ethanethionophosphonic acid ester.

* * * * *

UNITED STATES PATENT AND TRADEMARK OFFICE
CERTIFICATE OF CORRECTION

PATENT NO. : 4,014,996
DATED : March 29, 1977
INVENTOR(S) : Fritz Maurer, et al.

It is certified that error appears in the above-identified patent and that said Letters Patent are hereby corrected as shown below:

Col. 2, line 29      cancel "the" and substitute -- for --

Col. 4, line 28      cancel "kuehniella" and substitute --kuhniella--

Col. 4, line 66      cancel "Aedes" and substitute --Aëdes--

Col. 5, line 5      cancel "blackcurrent" and substitute --blackcurrant--

Col. 5, line 58      cancel "esters" and substitute --ethers--

Col. 16, compound C      cancel "$\text{>}\!-\!O\!-\!\overset{\overset{O}{\|}}{P}$" and substitute --"$\text{>}\!-\!O\!-\!\overset{\overset{S}{\|}}{P}$"--

Col. 17, compound 19      cancel "$-\!O\!-\!\overset{\overset{O}{\|}}{P}$" and substitute --"$-\!O\!-\!\overset{\overset{S}{\|}}{P}$"--

UNITED STATES PATENT AND TRADEMARK OFFICE
CERTIFICATE OF CORRECTION

PATENT NO. : 4,014,996
DATED : March 29, 1977
INVENTOR(S) : Fritz Maurer, et al.

It is certified that error appears in the above—identified patent and that said Letters Patent are hereby corrected as shown below:

Col. 21, compound 9    cancel "
$$\begin{matrix} O \\ \| \\ O\!\!-\!\!\!-\!\!P \end{matrix}$$
" and substitute $$\begin{matrix} S \\ \| \\ O\!\!-\!\!\!-\!\!P \end{matrix}$$
--

Signed and Sealed this

Sixth Day of September 1977

[SEAL]

Attest:

RUTH C. MASON
*Attesting Officer*

LUTRELLE F. PARKER
*Acting Commissioner of Patents and Trademarks*